United States Patent [19]

Magram

[11] Patent Number: 5,772,607
[45] Date of Patent: Jun. 30, 1998

[54] BODY FLUID COLLECTION APPARATUS

[75] Inventor: Gary Magram, Greenville, Del.

[73] Assignee: The Nemours Foundation, Jacksonville, Fla.

[21] Appl. No.: 471,274

[22] Filed: Jun. 6, 1995

[51] Int. Cl.$^6$ ........................................................ A61B 5/00
[52] U.S. Cl. ............................................................. 600/573
[58] Field of Search ................................... 604/118, 128, 604/246, 326, 164, 167, 317, 318, 319, 403, 410, 411; 128/76–771

[56] References Cited

U.S. PATENT DOCUMENTS

| | | | |
|---|---|---|---|
| 3,654,924 | 4/1972 | Wilson et al. | 128/214 D |
| 3,704,709 | 12/1972 | Sorenson et al. | 128/277 |
| 3,785,367 | 1/1974 | Fortin et al. | 128/2 F |
| 3,957,050 | 5/1976 | Hines, Jr. | 128/275 |
| 4,060,107 | 11/1977 | Naftulin | 141/7 |
| 4,522,623 | 6/1985 | Lauterjung | 604/319 |
| 4,645,486 | 2/1987 | Beal et al. | 604/4 |
| 4,675,010 | 6/1987 | Siposs et al. | 604/319 |
| 5,122,121 | 6/1992 | Sos et al. | 604/167 |
| 5,167,656 | 12/1992 | Lynn | 604/409 |
| 5,207,661 | 5/1993 | Repschlager | 604/317 |

Primary Examiner—Max Hindenburg
Assistant Examiner—Pamela L. Wingood
Attorney, Agent, or Firm—J. Michael Martinez de Andino; McGuire, Woods, Battle & Boothe LLP; Jeffrey C. Lew

[57] ABSTRACT

A sample container and a fluid collection apparatus are disclosed for withdrawing samples for fluid analysis purposes of unpressurized body fluid from an internal body cavity. The container and apparatus are primarily useful for sampling cerebrospinal fluid obtained through a lumbar puncture or shunt tap. The container and apparatus provide a completely enclosed sample environment which protects the sample from external contamination during the sample-taking process. The enclosed environment also protects sample-taking personnel against direct contact with the fluid. The novel sample container includes an inflatable pouch with a balloon that expands on filling without significantly raising back pressure on the fluid draining from the patient. The pouch is affixed within a transparent, rigid sheath by an inlet port. The apparatus includes a needle assembly with an internal rubber septum. The septum prevents fluid from leaking out when a stylet is removed from the needle bore after the lumbar puncture is performed.

16 Claims, 5 Drawing Sheets

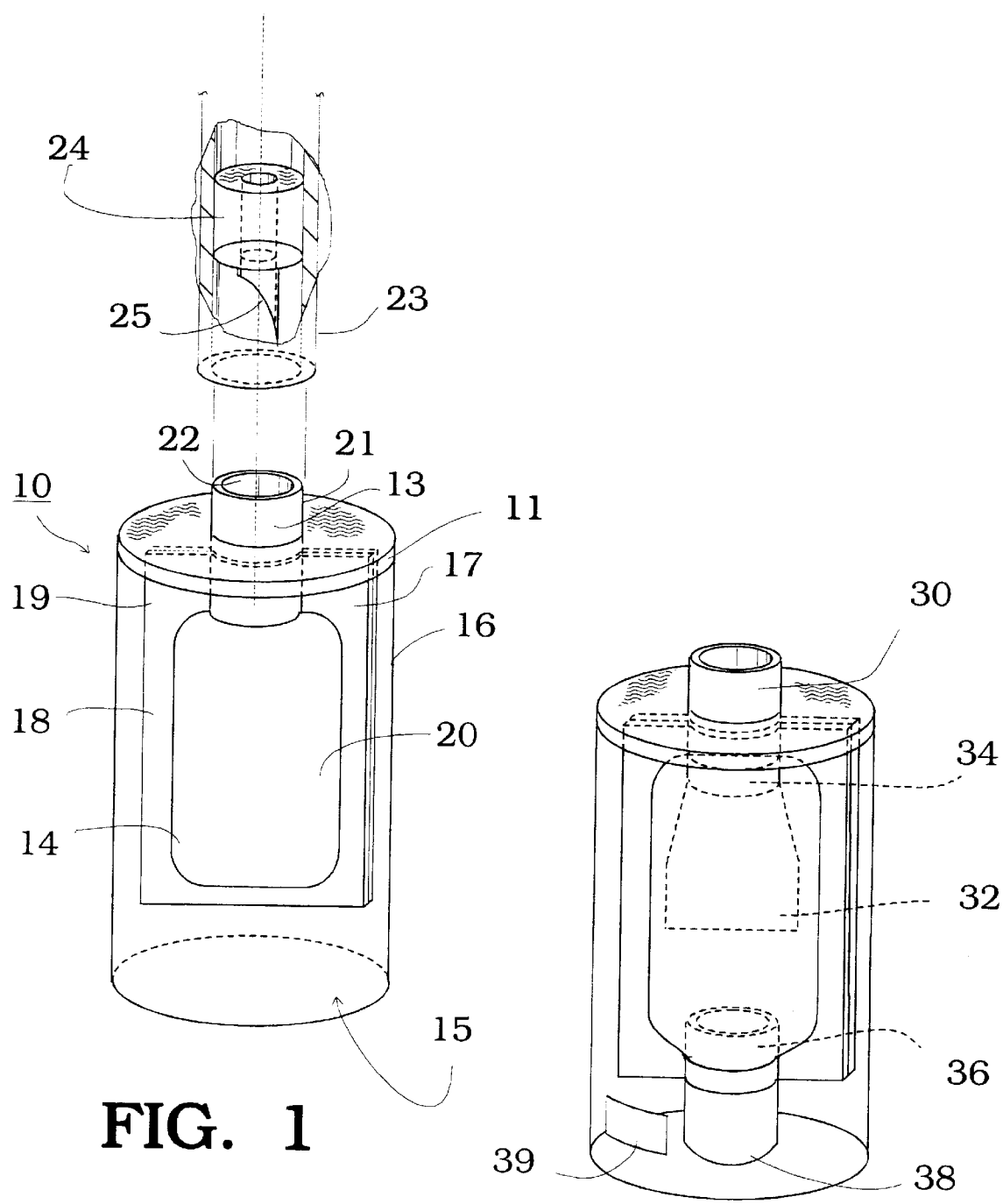

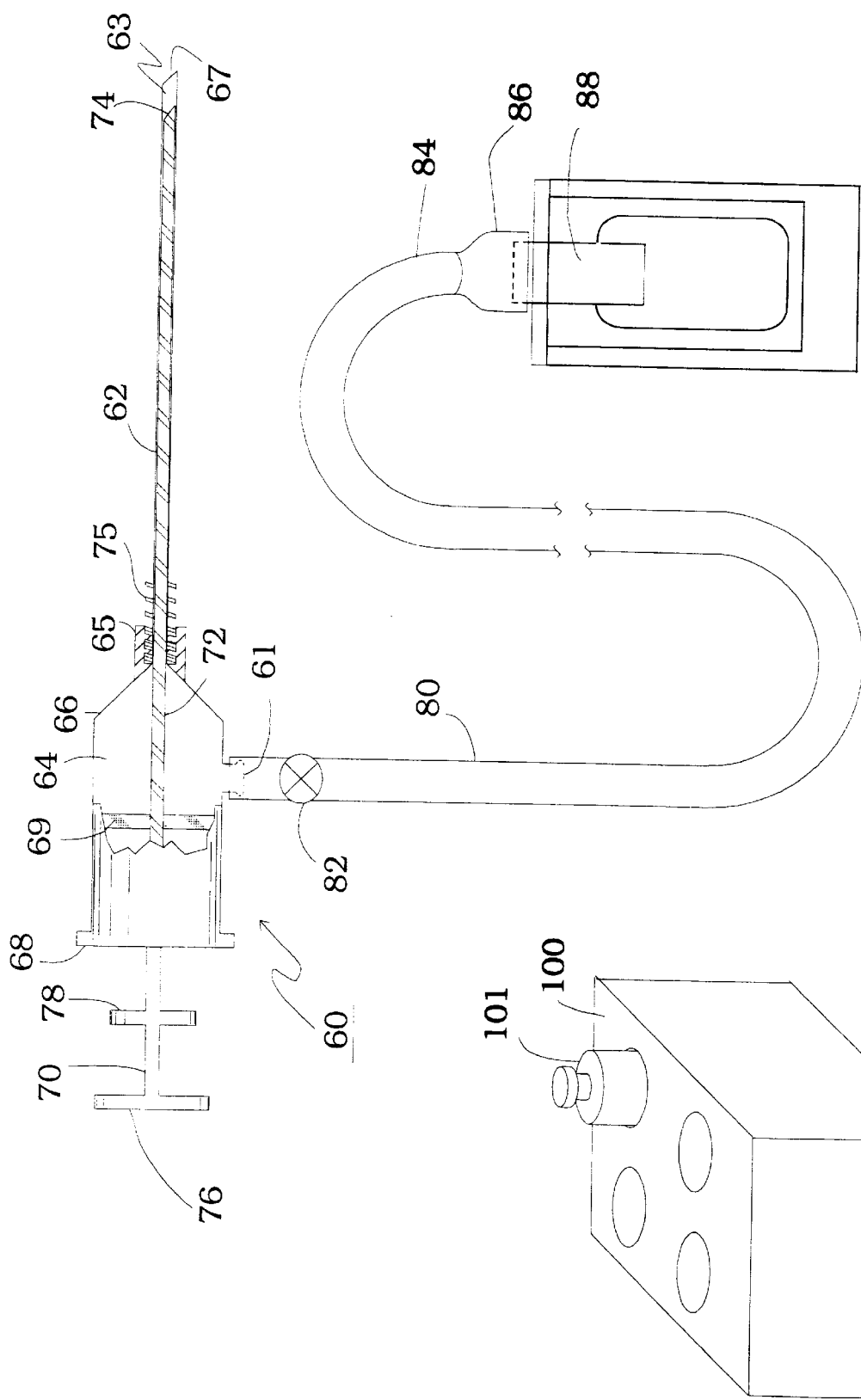

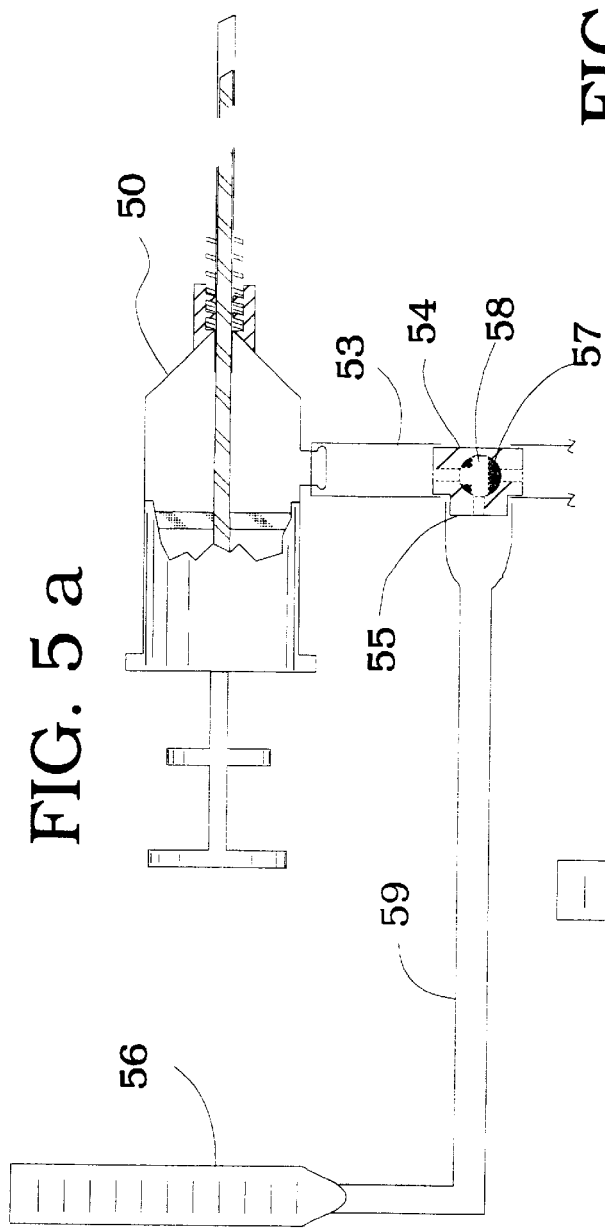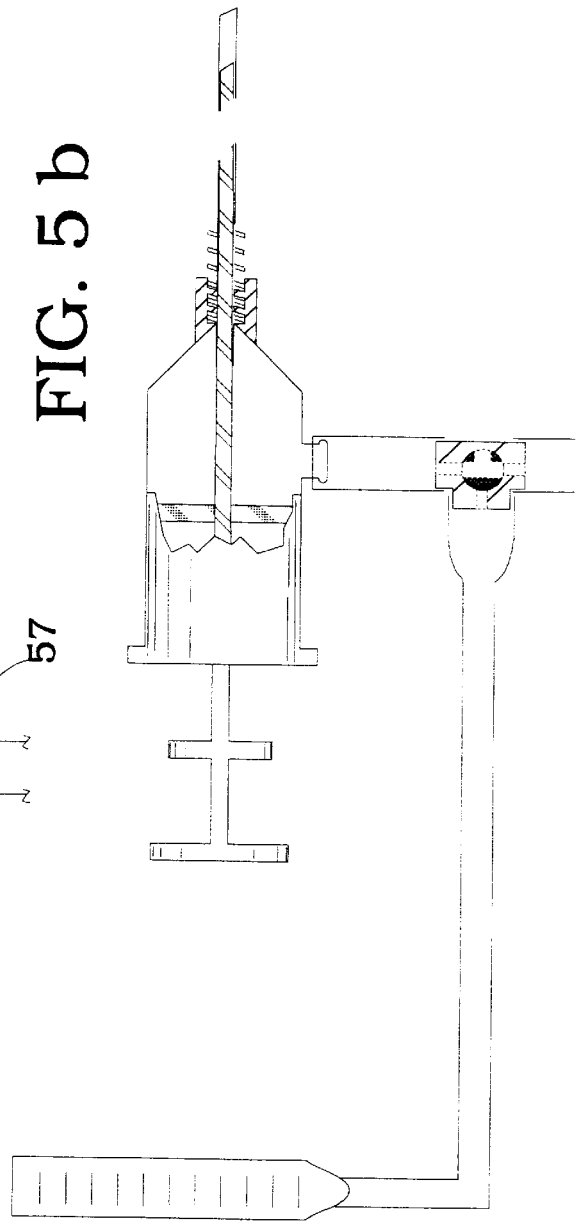

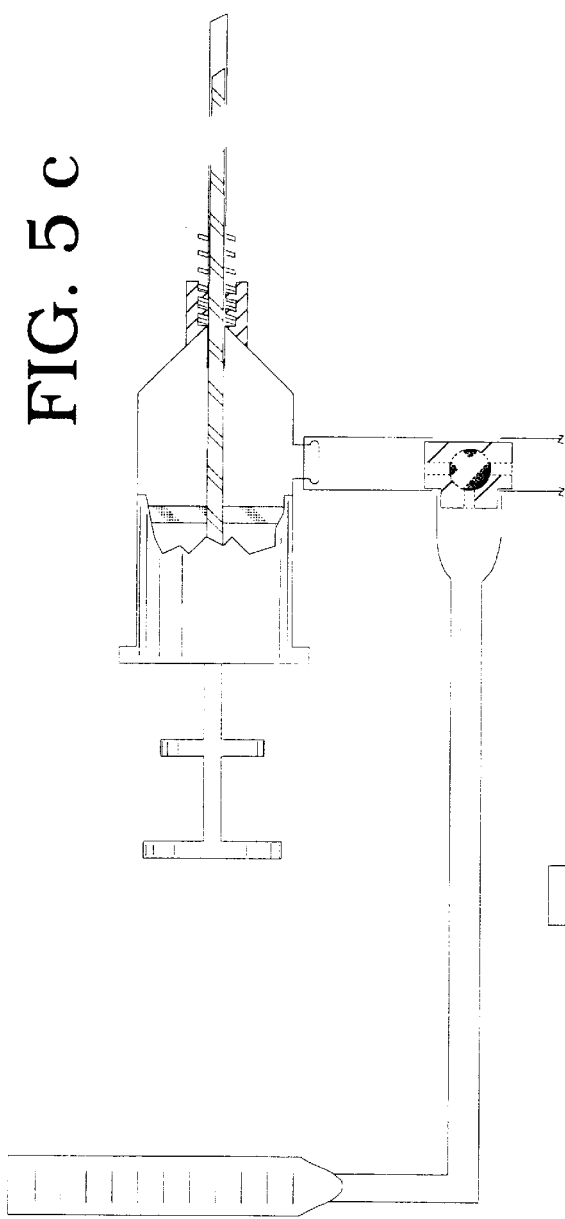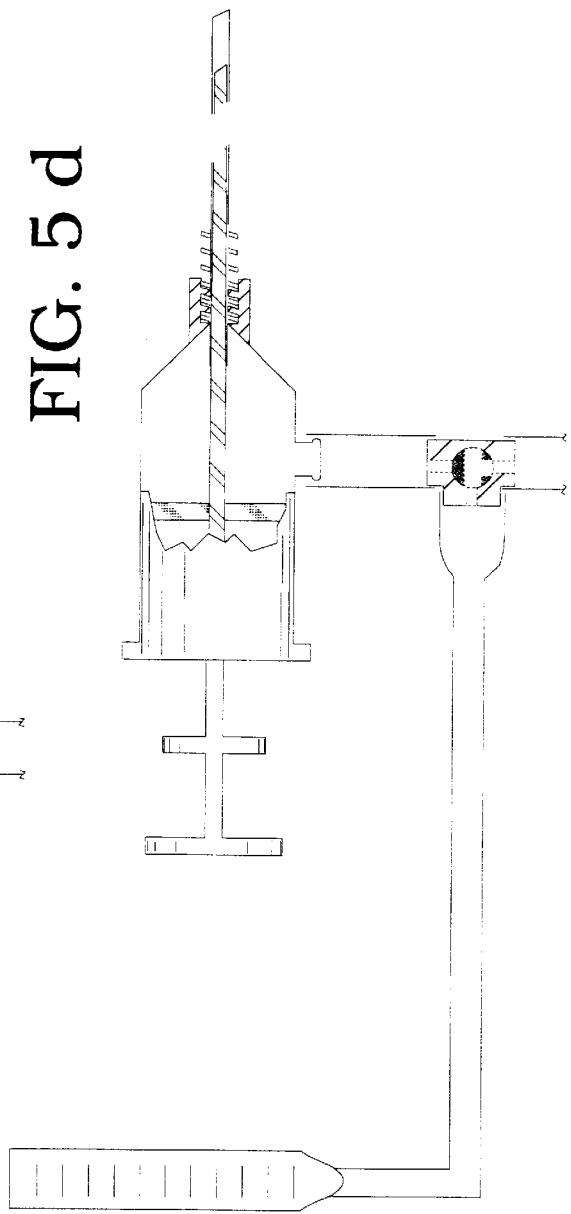

BODY FLUID COLLECTION APPARATUS

FIELD OF THE INVENTION

This invention relates to an apparatus for removing fluid from a cavity within the body. More specifically, the invention relates to a sample container for cerebrospinal fluid drawn through a lumbar puncture or spinal tap.

BACKGROUND AND SUMMARY OF THE INVENTION

A common method for obtaining a sample of cerebrospinal fluid (CSF) for analysis includes drawing the fluid by way of a lumbar puncture or shunt tap. Generally, the CSF flows through a needle to a flexible tube, from which the fluid is permitted to drain into a sample container.

CSF will not flow through the tube against more than slight back pressure because the fluid within the shunt or lumbar dural sacs is unpressurized. Therefore, the tube cannot be drained into a conventional, sealed, non-subatmospheric pressure container. Any fluid introduced into a sealed container compresses the vapor inside the container which raises the pressure above the pressure within the sacs, thereby stopping fluid flow. It is recognized that CSF removal under vacuum, for example with a syringe, can be detrimental to the patient. For example, vacuum withdrawal of fluid from a shunt can aspirate choroid plexus or other debris into the proximal ventricular catheter. Also, vacuum withdrawal of CSF from a lumbar dural sac can aspirate and traumatize a nerve root. Hence, the generally approved sampling technique thus involves "open air" draining of the fluid from the end of the tube into an open sample container.

This technique has the drawback that the fluid can easily become contaminated either by exposure to the environment as it passes through ambient air between the tube and the sample container, or from contamination of the open sample container by the person doing the sampling. Coincidentally, the pathogens usually sought to be identified or quantified by analysis of CSF are frequently prevalent in the sampling room atmosphere. Hence redundant samples or other similarly painful and/or costly procedures are typically used to remove doubts concerning false positive analytical determinations obtained by open air sampling.

Open air sampling also suffers from the drawback that attending medical personnel or the work area can be contaminated by the patient's body fluid. Open air sampling of CSF typically presents substantial opportunity for spilling fluid and contaminating medical personnel. For example, the sampling person holds the end of the tube in one hand and the container below it in the other hand. The sampling person usually is bent over because the tube end must be below the patient, who is normally lying on a table, for the fluid to drain by force of gravity. Additionally, the patient, particularly a child feeling discomfort during the procedure, is likely to squirm and wriggle. This body movement, awkward positioning and the small diameters of the tube and container often make holding the tube end directly over the container to avoid spilling or splashing the fluid difficult. The lumbar puncture apparatus commonly used to withdraw CSF from a patient also provides opportunity for contaminating the sampling person. A lumbar puncture procedure normally requires piercing the body with a long needle, the lumen of which is temporarily filled with a stylet. After the needle is fully inserted, the stylet is withdrawn allowing CSF to flow through the lumen to a receiving vessel outside the body. Generally, in order to measure CSF pressure, the stylet is completely removed and a manometer is connected to the stylet entrance hole. Conventional lumbar puncture instruments allow the fluid to leak from the hole as the stylet is removed. This leakage can contaminate the sampling person and at least partially vents CSF pressure such that an accurate pressure determination frequently cannot be obtained.

It is well recognized that certain life threatening diseases, for example, acquired immune deficiency syndrome (AIDS), are transmitted through contact with body fluid of an infected person. Therefore, the possibility of contaminating medical personnel with the patient's body fluid is realistic and the consequences can be serious.

Accordingly, it is an object of the present invention to provide a CSF sampling apparatus which overcomes the disadvantages identified above. More particularly, it is an object to provide a CSF sampling container which substantially reduces the risk of contaminating the sample with pathogens or other agents present in the sampling environment that could interfere with sample analysis. Samples taken with the novel container should be less susceptible to false positive determinations because the container is completely sealed from outside exposure. Thus the novel container provides the advantages that analyses are more reliable; fewer redundant samples are needed; and pain and costs associated with sample analysis are reduced.

Another object of the invention is to provide a CSF sampling apparatus that reduces the risk to medical personnel from contact with potentially disease containing body fluid. The novel sample container and apparatus present the advantage that CSF samples can be drained into a sealed containment vessel through a completely contained transfer system by gravity in the absence of other fluid motivation force. Consequently, the container according to the present invention prevents exposure by medical personnel and the work area, e.g., clothing and environmental surfaces, because the sample is not exposed to open air. The novel sampling apparatus further provides the beneficial feature that CSF should not leak out when the stylet is removed.

Accordingly, there is now provided in drawing from within a patient's body cavity of a sample of an unpressurized body fluid for analysis, a sample container, comprising:
 a rigid, transparent sheath defining an enclosure vented to atmospheric pressure outside the sheath; and
 an inflatable pouch to receive body fluid, the pouch including:
  a balloon within the enclosure defining an inner space and having an outer surface exposed to pressure within the enclosure and outside the pouch; the balloon being, capable of free inflation within the enclosure as unpressurized body fluid drains by gravity in the absence of other fluid motivation force into the inner space; and an inlet port joined to the balloon and in fluid communication with the inner space and adapted to provide a detachable, fluid tight connection to a source of supply of unpressurized body fluid, the inlet port being affixed to the sheath.

The present invention further provides in drawing from within a cavity of a patient's body of a sample of an unpressurized body fluid for analysis, a sealed, non-subatmospheric pressure, fluid collection apparatus, comprising:
 (a) a sample container, comprising:
  a rigid, transparent sheath defining an enclosure vented to atmospheric pressure outside the rigid, transparent sheath; and an inflatable pouch within the enclosure to receive body fluid, the inflatable pouch including:

a balloon within the enclosure defining, an inner space and having an outer surface exposed to pressure within the enclosure and outside the inflatable pouch; the balloon being capable of free inflation within the enclosure as unpressurized body fluid drains by gravity in absence of other fluid motivation force into the inner space; and an inlet port joined to the balloon and in fluid communication with the inner space and adapted to provide a detachable, fluid tight connection to a source of supply of unpressurized body fluid, the inlet port being affixed to the rigid, transparent sheath;

(b) a needle assembly adapted to communicate with the cavity and conduct body fluid outside the patient's body, the needle assembly including:

a hollow barrel with an open end and a wall structure defining an interior volume to accept the body fluid;

an elastomeric septum within the hollow barrel defining a puncturable, self-sealing, wall separating the interior volume from the open end;

an outlet port on the wall structure and adapted to export body fluid from the interior volume, (c) a transfer tube having first and second ends, the transfer tube being close coupled at the first end in fluid communication with the outlet port, and the tube including at the second end an adapter means for detachably, fluid tightly connecting the second end to the sample container; and (d) a block valve between the cavity and the sample container for reversibly interrupting flow through the transfer tube.

There is also provided a process for drawing under gravity induced flow in the absence of other fluid motivation force, a sample of an unpressurized body fluid into a sealed, non-subatmospheric sample container via a fluid collection apparatus.

BRIEF DESCRIPTION OF THE DRAWINGS

FIG. 5a is a fluid collection apparatus with a block valve in the transfer tube wherein the three-way stopcock is in the measure pressure position.

FIG. 5b is the fluid collection apparatus of FIG. 5a with the three-way stopcock in the fill sample position.

FIG. 5c is thee fluid collection apparatus of FIG. 5a with the three-way stopcock in the stop flow position.

FIG. 5d is the fluid collection apparatus of FIG. 5a with the three-way stopcock in the drain manometer position.

DETAILED DESCRIPTION

The sample container of the present invention provides a completely sealed, non-subatmospheric pressure, aseptic receptacle for collection of body fluid, especially fluid which is unpressurized while resident within the body. For the purpose of this disclosure, the term "unpressurized" means that the fluid is at low pressure and that the body is not physiologically able, by itself, to motivate expulsion of the fluid from a source reservoir to an external sample container. An unpressurized fluid can be withdrawn from the body by gravity or by an externally applied fluid motivating force, such as aspiration under vacuum. By comparison, blood in the circulatory system at pressure developed by the heart, is an example of a pressurized fluid. Although the novel sample container is suitable for use with pressurized body fluid, a primary purpose of the invention is to facilitate the collection of unpressurized body fluids. Cerebrospinal fluid (CSF) is an example of such an unpressurized body fluid to which the development of the present invention is directed. The novel sample container is particularly useful for obtaining small quantities of such fluid for analytical purposes.

Figures 1, 2:
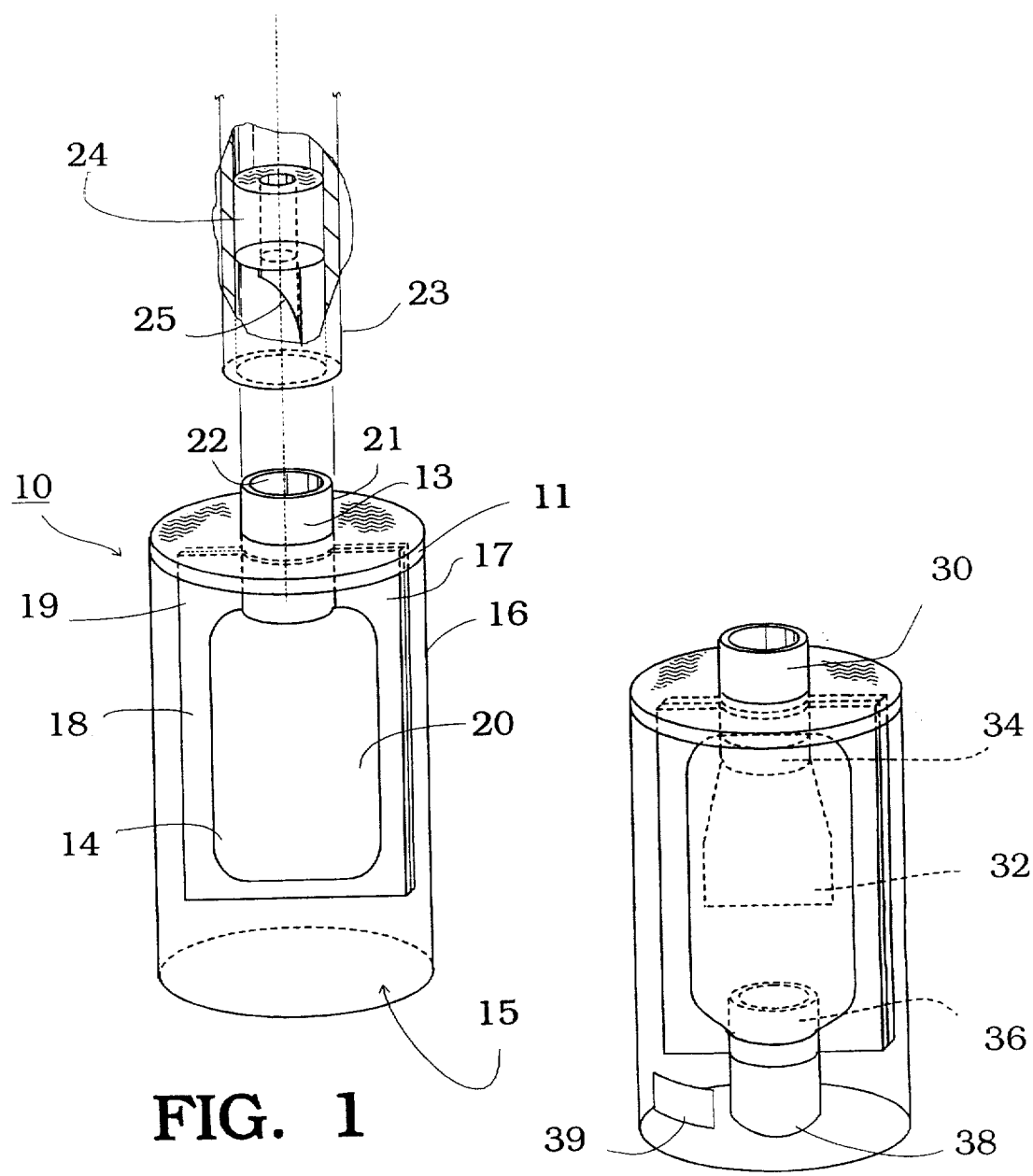
FIG. 1 is a perspective view of a sample container according to the present invention.
FIG. 2 is a perspective view of another embodiment of a sample container according to the present invention.

A basic embodiment of the novel sample container 10 can be well understood with reference to FIG. 1. Body fluid is received by an inflatable pouch 14 in a rigid sheath 16. Preferably, the sheath is transparent so that the progress of filling the pouch can be visually observed. Any of the commercially available, clear engineering plastic polymers should be suitable for this purpose. The sheath defines an enclosure that is vented to atmospheric pressure in the work area outside the sheath. The sheath shown in FIG. 1 is a completely closed cylinder except for an open bottom 15. The sheath can be another shape and can have other openings to the outside. For example, the sheath could be a perforated box or an otherwise closed container with a vent port for equalizing inside and outside pressures.

The pouch has an inlet port 13 which can extend outside the sheath, for admitting fluid into the balloon portion 14 within the sheath. The inlet port has flange 11 to connect the pouch to the sheath. The flange can be glued, bolted or screwed, i.e., like a cap on a jar, to the sheath, for example. The balloon is constructed of generally thin, preferably transparent, flexible sheets 17. Other methods of attaching the inlet port or the fluid entrance part of the balloon portion to the sheath should be readily apparent to one of ordinary skill in the art. For example, the outside surface of the walls of the balloon portion defining a rim can be glued to the inner surface of the sheath. The balloon walls are constructed to enable the balloon to freely inflate as fluid enters the pouch and accumulates therein. Preferably, the balloon has elasticity that lets the walls distend to increase the volume of the inner space inside the balloon, while exerting at most only negligible back pressure on the fluid. The outer surface of the balloon is exposed to the pressure inside the sheath and outside the pouch. Because the sheath enclosure is vented to outside atmosphere, back pressure on the fluid does not build as fluid accumulates in the pouch.

The inlet port selves several purposes. It provides a passage way through the sheath for incoming fluid to enter the balloon. It also attaches the pouch to the sheath so that the balloon remains inside the sheath. The sheath thus becomes a convenient handle for holding the pouch. A pouch without a rigid sheath should be suitable for CSF sampling. However, the sheath protects the pouch from accidental puncture by nearby sharp objects. The sheath also protects against the sampling person holding the pouch too tightly and thereby exerting excessive back pressure on the fluid. The sheath design illustrated in FIG. 1, for example, also provides a support which allows the sample container to stand freely on any convenient flat, horizontal surface. The sheath or inlet port can optionally be equipped with hooks, flanges or similar appendages adapted to hold the sample container in a sample storage apparatus while awaiting or during fluid analysis. In a preferred embodiment, the sheath has dimensions adapted to fit a conventional analytical centrifuge so that the fluid sample call be centrifuged directly in the pouch without the need for transfer to a centrifuge tube. The inlet port further serves to mate the sample container with a corresponding connector of a fluid delivery apparatus to provide a fluid tight, detachable connection to a source of CSF.

The balloon can be produced by conventional methods. For example, as shown, two adjacent sheets of film are circumferentially laminated in a peripheral region 18 leaving an unlaminated, central pocket 20 which defines an initially collapsed inner space. Lamination can be accomplished by thermal or adhesive sealing. The sheets preferably are of high temperature resistant, organic polymers which enable the pouch to be sterilized prior to use. Prior to laminating, the tubular inlet port 13 is inserted between the sheets which can be joined to the inlet port by thermal or adhesive sealing methods, for example. The pouch can also be formed by molding. The inlet port comprises a rigid hollow tube nipple 21 and preferably includes an optional elastomeric cap 22 covering the lumen. The elastomeric cap is a puncturable, self-sealing membrane which keeps the pouch closed until ready for use, thereby reducing the risk of contamination. CSF from a source of supply, such as the apparatus discussed below, can be introduced into the pouch through an elastomeric transfer tube 23, having a suitable inner diameter to make a fluid tight connection by sliding the tubing over the tube nipple 21. The point 25 of piercing nozzle 24 previously inserted in the lumen of the transfer tube will puncture the elastomeric cap when the tube is connected to the nipple to allow fluid to flow into the pouch. The elastomer in the cap is chosen to be sufficiently elastic that as the point of the piercing nozzle is withdrawn when the tube is disconnected from the nipple, the cap will close the puncture hole to maintain a barrier against contaminating or spilling the fluid.

FIG. 2 illustrates a sample container according to the present invention wherein the inlet port 30 additionally includes a flap type check valve 32 to prevent inadvertent reflux emission of the fluid from the pouch back through the inlet port. The valve is a flexible polymer tube having a normally flat lumen, as made, for example, by overlaying two strips of film and sealing the strips together along both long edges to leave a flat tube running the length of the strips. One end of the flat lumen tube is slipped over an internal extension of the inlet port 34 and sealed thereto to make a fluid tight connection. The flat lumen tube can be clamped, glued or thermally sealed to the extension, for example. Normally, the flap valve is closed because the two strips of the check valve at the end of the tube within the balloon are adjacent each other. Fluid from the balloon cannot pass into the flat lumen to escape through the inlet port. However, the strips will allow fluid to enter the balloon when fluid drains into the inlet port from a CSF source. At such times, the pressure between the strips will exceed the pressure in the balloon and will cause the strips to separate. When flow into the pouch is stopped, the film strips will revert to the closed position, thereby sealing off the inlet port from any back flow. A ball check valve could also be used to prevent back flow.

FIG. 2 further illustrates the optional discharge means feature of the novel sample container. This feature addresses the desire to carefully extract a fluid sample from the sample container. A discharge nozzle 36 is located at a location on the balloon convenient for removing fluid, i.e. near the vent opening in the sheath. The discharge nozzle shown is a rigid tubular fitting terminating in a closed ended tubing nipple 38. After drawing the CSF sample from the patient, the container can be removed to an analytical facility for analysis. There the end of the tubing nipple can be cut away or punctured with a piercing nozzle for example. Then a tube connected to the analytical apparatus can be connected to the tubing nipple to extract a sample from the container. Alternatively, the discharge nozzle can include a screw fastened cover, i.e., a removable cap, to permit the sample to pour from the container, or a rubber septum across the lumen of the discharge nozzle to provide syringe access to the fluid in the pouch.

The sample container of this invention is primarily intended for collecting small samples of unpressurized body fluid for analytical purposes. Consequently, the size of the container normally will be commensurate with small fluid sample sizes. It is contemplated that novel CSF sample containers preferably have inflatable pouches of 2, 5, and 10 ml capacity. It is further understood that frequently multiple samples of CSF are taken from a patient, each sample for a different analysis. The analyses usually require that the samples are treated differently. Conventional CSF sample kits do not provide containers for easily distinguishing between CSF samples intended for different analytical treatments, Hence, the likelihood of improperly preparing a CSF sample for analysis is significant. It is a feature of the present invention that sample containers can be provided with a color coded identification tag 39 on the sheath for simple identification of the purpose of the sample. For example, a purple tag could indicate a sample for cell count or hematology analysis; a red tag could indicate chemical analysis; a yellow tag culture and sensitivity analysis and a green tag cytology analysis.

Figures 3, 6:
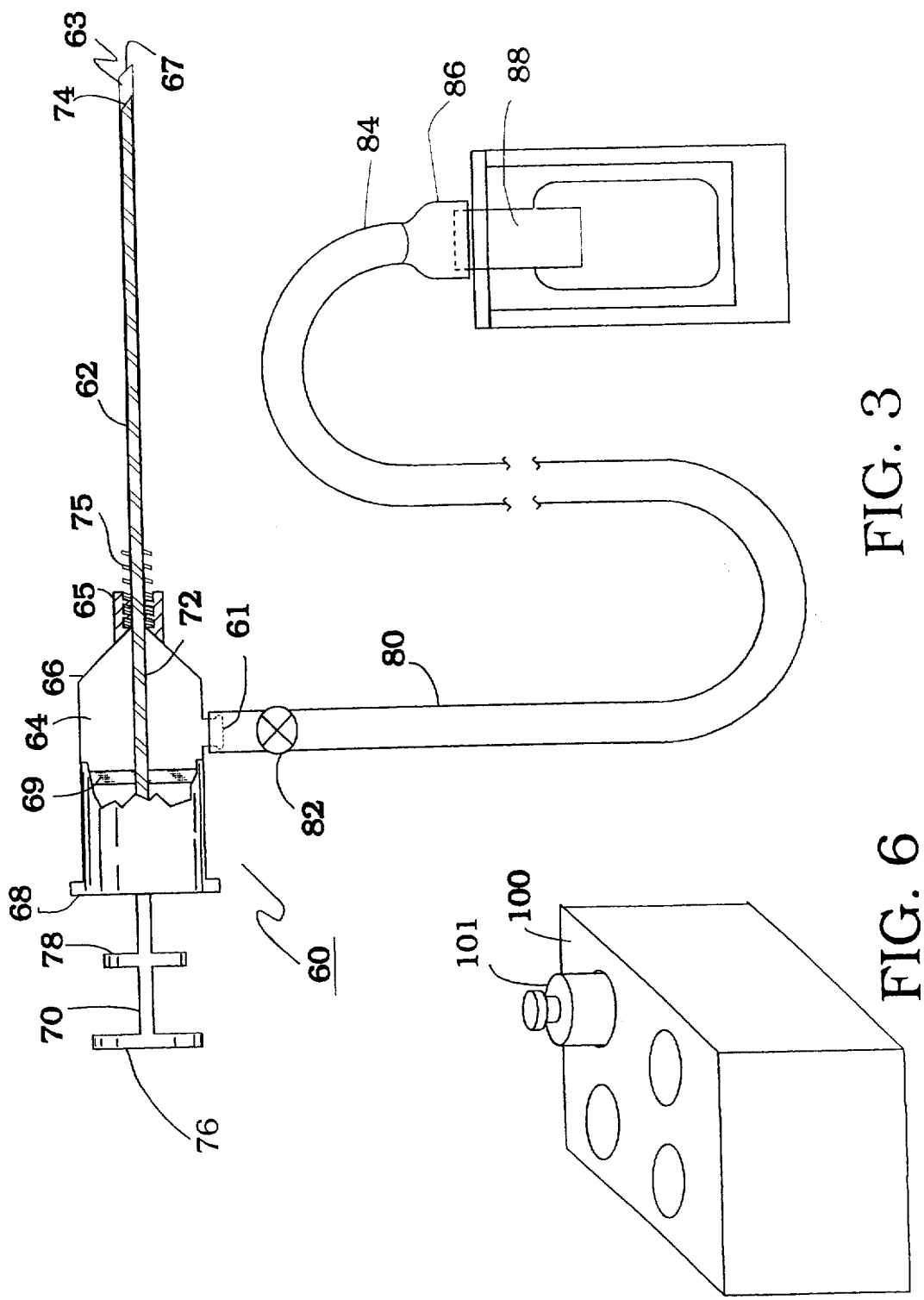
FIG. 3 is a partially cutaway elevation view of a fluid collection apparatus of the present invention.
FIG. 6 is a perspective view of a sample container holding device.
Figure 4A:
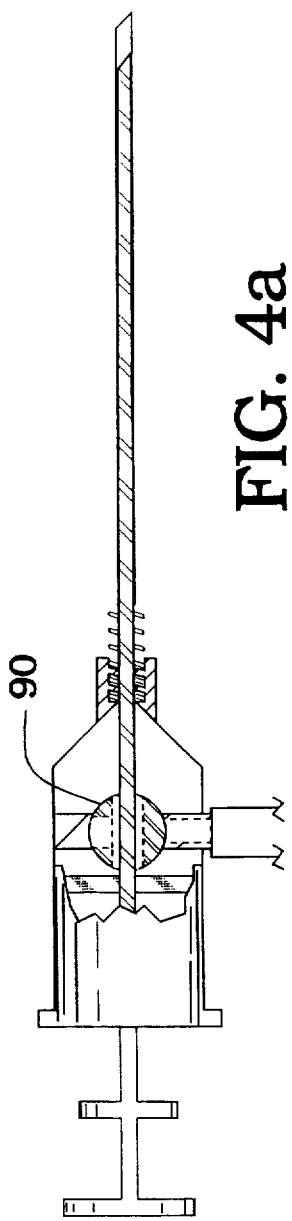
Figure 4B:
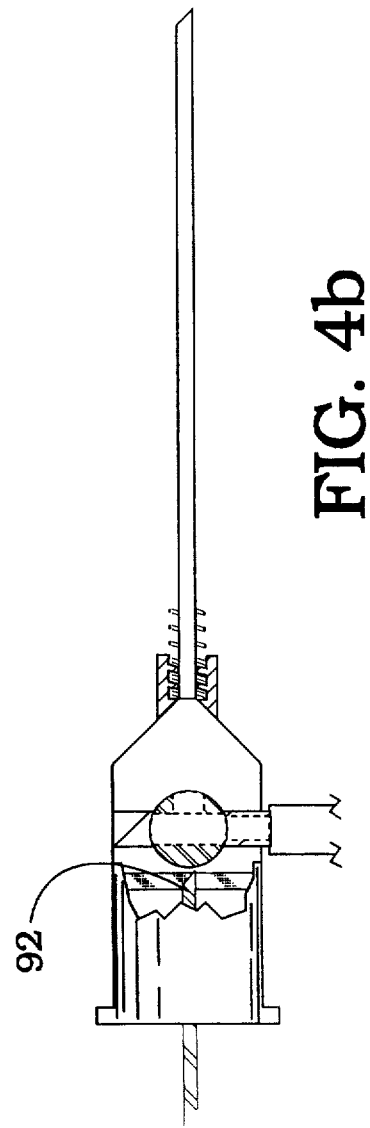
Figure 4C:
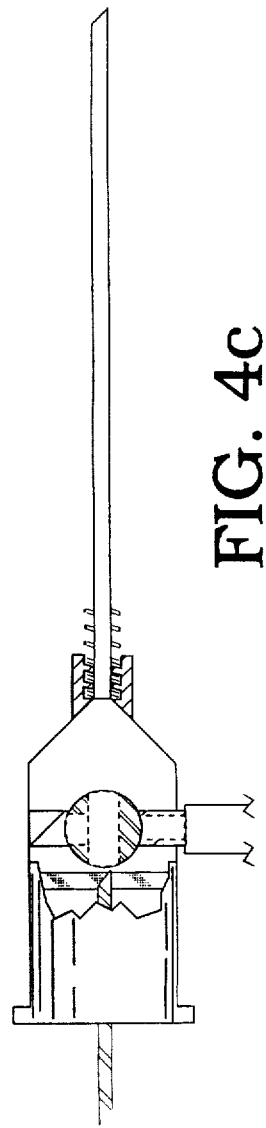

The novel sample container described above is particularly used to advantage in connection with a fluid collection apparatus 60 according to this invention, FIG. 3. The fluid is retrieved usually by penetrating the patient's back with a suitably long and strong needle 62 to pierce the dural sac surrounding the spine. The needle is mounted in fluid communication with the interior volume 64 of a rigid, hollow barrel 66. The barrel is preferably transparent to permit visual identification of the fluid and verification of fluid flow. Because the axial bore 63 of a spinal needle is typically large, body tissue can enter and occlude the bore when the needle is inserted. A stylet 70 is thus extended through an open end of the hollow barrel to plug the bore during needle insertion. After needle insertion, the stylet is removed from the axial bore to permit CSF to drain into the interior volume. The stylet comprises of a straight rod 72 with a tip 74 at a sharp, pointed end, and a handle 76 at the other end. The rod cross section is geometrically similar to the cross section of the bore. Preferably the rod and bore are circular. The rod cross section is slightly smaller than that of the bore to enable easy insertion into and withdrawal from the bore. The stylet tip preferably is shaped similarly to the needle tip 67 in order that the stylet completely plugs the bore when driven fully into the needle. The rod can include a stop 78 affixed at a distance from the tip predetermined to contact the end face 68 of the barrel when the stylet is fully inserted in the bore. The needle is removably attached to the nose 65 of the barrel with a screw thread fitting 75 or equivalent mechanism. This permits changing needles to meet the needs of different patients or for connecting to a shunt tap. Naturally, corresponding, stylet dimensions are selected to fit the needle according to the principles previously described. A stylet is not normally used for a shunt tap.

An elastomeric septum 69 within the hollow barrel defines a puncturable, self-sealing wall to separate the interior volume from the open end. The septum provides a bearing for the stylet as well as a fluid barrier. That is, when the stylet rod punctures the septum to enter the needle bore, the septum elastically closes around the surface of the rod which confines the fluid within interior volume 64 and prevents fluid leaks or contamination across the septum. The novel fluid collection apparatus thus provides the great advantage over conventional instruments that body fluid does not leak from the hole in the end face of the barrel when the stylet is withdrawal.

CSF leaves the interior volume for delivery to the sample container by way of an outlet port 61 through the barrel wall. The outlet port 61 can be a tubing nipple adapted to mate with one end of a flexible, but non-collapsable, transfer tube 80. That is, the tube can be occluded by compression with sufficient force, however, it should be capable of remaining unobstructed when flexed during fluid transfer. The transfer tube is of rubber or plastic. The tubing nipple size and inner diameter of the transfer tube are selected to provide a fluid tight seal by slipping the transfer tube end over the outlet port. The seal between the outlet port and the transfer tube thus prevents contamination or leakage of the fluid. The tube can be clamped to the outlet port to further guard against inadvertent separation of the tube from the port. Alternatively, the transfer tube can couple to the outlet port by a screw connection. In still another configuration, the transfer tube can be a permanently attached extension of the outlet port.

The fluid collection apparatus additionally includes a block valve 82 between the fluid source, i.e., the body cavity and the sample container. The purpose of the block valve is to temporarily interrupt flow. Frequently, multiple samples of CSF are taken from a patient in rapid succession. A block valve allows the sampling person to temporarily stop flow in order to replace a filled sample container with a fresh, empty one, and then to restart flow. The block valve 82 can be a simple pinch mechanism, such as a hemostat or a pinch clamp that squeezes the transfer tube. An in line, mechanical valve, such as a ball valve is also suitable.

A three-way valve as illustrated in FIGS. 5*a*–5*d* can be used as a block valve with added capability of measuring CSF pressure periodically during sampling. FIG. 5*a* shows a needle assembly 50 connected to a transfer tube 53 including three-way valve 54, in section view. Side arm nipple 55 provides a connection to manometer 56 for measuring CSF pressure. The stopcock 57 includes a T-shaped channel 58 for diverting flow. In FIG. 5*c* stopcock 57 is in blocked flow position. Fluid in the needle assembly is blocked from flowing to the sample container. Stopcock position shown in FIG. 5*b* allows flow from the needle assembly to the sampler container. In order to measure the patient's CSF pressure, the stopcock is rotated to the position of FIG. 5*a*. This permits fluid to enter the manometer without spilling fluid. In FIG. 5*d*, only fluid in the manometer from a previous pressure determination is permitted to drain into the transfer tube where it can be collected for analysis in a sample container or discarded. Transfer tube 53 and manometer tube 59 diameters should be as small as possible to reduce the fluid resident therein to a minimum. Inner diameter of about 1 mm is preferred.

Figure 4A:
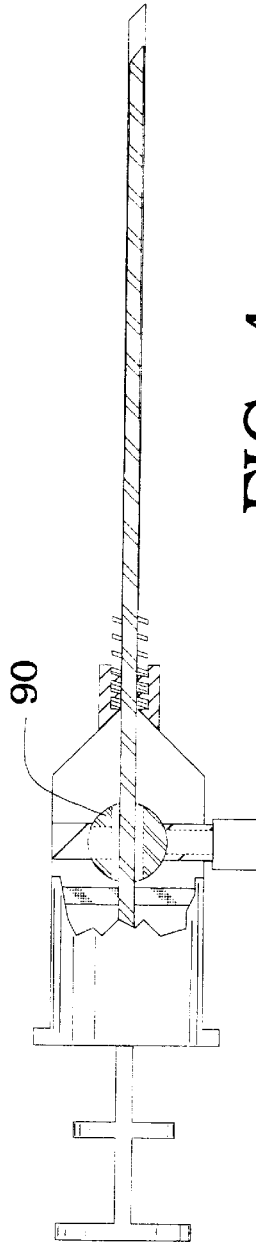
FIG. 4a is a partially cut away view of a fluid sampling apparatus with a three-way stopcock inside the body of the needle assembly in the stylet inserted position.
Figure 4B:
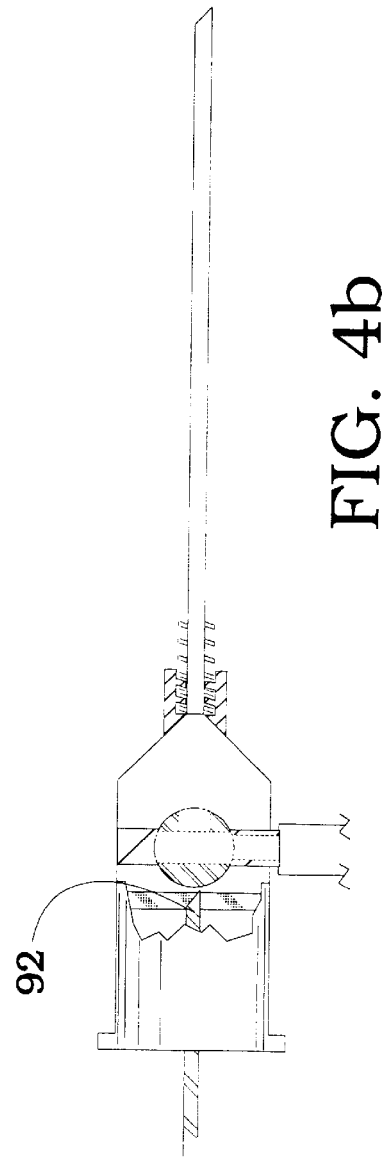
FIG. 4b is a partially cut away view of the fluid sampling apparatus of FIG. 4a, with the three-way stopcock in the fill sample position.
Figure 4C:
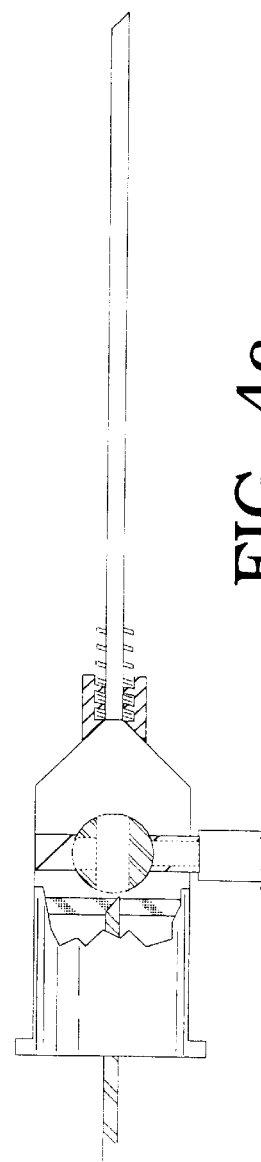
FIG. 4c is a partially cut away view of the fluid sampling apparatus of FIG. 4a, with the three-way stopcock in the stop flow position.

FIGS. 4*a*–4*c* illustrate a fluid collection apparatus according to the present invention which employs a three-way stopcock 90 block valve inside the hollow barrel. In preparation for inserting the needle into the patient, the stopcock is placed as shown in FIG. 4*a* to permit passage of the stylet. After inserting the needle and removing the stylet, 92, the stopcock is rotated to the position of FIG. 4*b* which establishes CSF flow from the interior volume to the transfer tube. When necessary to stop flow to the sample container, the stopcock is rotated to the position shown in FIG. 4*c*. To reestablish flow, the stopcock can be returned to the position of FIG. 4*b*.

Referring, to FIG. 3, the second end 84 of the transfer tube has an adapter 86 designed to mate with the inlet port of the sample container described above. The adapter will make a positive, fluid tight, but easily detachable connection to the sample container. Various adapter types, such as screw-on, snap-on, slip-on, i.e. tube and nipple, and clamped fittings are suitable.

The fluid collection apparatus and sample container according to the present invention can be used to obtain samples for analysis of CSF as follows. An empty deflated sample container is connected in a fluid tight manner to the second end of the transfer tube of a fluid collection apparatus as shown in FIG. 3. A needle 62 of proper diameter and length to penetrate the dural sac of the patient is placed on hollow barrel 66. A stylet 70 matched to the selected needle geometry is inserted into the needle assembly and the tip is forced through septum 69. The stylet is pushed into the axial bore until stop 78 abuts end face 68. Block valve 82 is opened to connect interior volume 64 of the hollow barrel with the inner space of the sample container. The sampling person effects a lumbar puncture. With the needle tip 67 maintained immersed the body fluid, the stylet is removed from the axial bore to permit fluid to drain into the interior volume of the hollow body. The stylet can be completely withdrawn from the hollow barrel without fluid leaking from the open end. The sample container is placed at an elevation below the patient sufficient to permit the body fluid to drain through the transfer tube 80 into the inflatable pouch. While filling, the sample container can be in any position, although the rigid sheath should allow the sample container to stand freely on a horizontal flat surface in the upright position shown in FIG. 3. An optional sample container stand 100, FIG. 6, adapted to hold upright the container 101 shown capped can be used. As fluid enters the pouch, the balloon expands to occupy an increasing fraction of the enclosure inside the sheath. Air in the enclosure and outside the pouch is vented outside the sheath so that back pressure on the fluid does not increase as the pouch fills. Fluid continues to drain into the pouch until an adequate sample has accumulated. Block valve 82 is closed, causing flow through the transfer tube to stop. If the block valve is not closed, fluid flow into the pouch and expansion of the balloon will continue until the outer surface of the balloon contacts the wall of the sheath. The rigid sheath wall prevents further expansion of the balloon and thus automatically stops flow. The filled sample container is disconnected and can be capped to prevent contamination. If an additional sample is desired, another empty sample container can be connected to the second end of the transfer tube and flow started again by opening the block valve.

To measure CSF pressure, a pressure sensor and three-way valve as in FIGS. 5*a*–5*d* can be used. Flow is stopped, FIG. 5c, and an appropriate container is connected to the second end of the transfer tube. The valve is turned to position of FIG. 5a to allow fluid to reach the pressure sensor for measurement. Next, the sensor fluid is drained, FIG. 5d. Then the container can be replaced with a sample container and flow restarted, FIG. 5b, to collect a sample.

Although specific forms of the invention have been selected for illustration in the drawings, and the preceding description is drawn in specific terms for the purpose of describing these forms of the invention, this description is not intended to limit the scope of the invention which is defined in the claims.

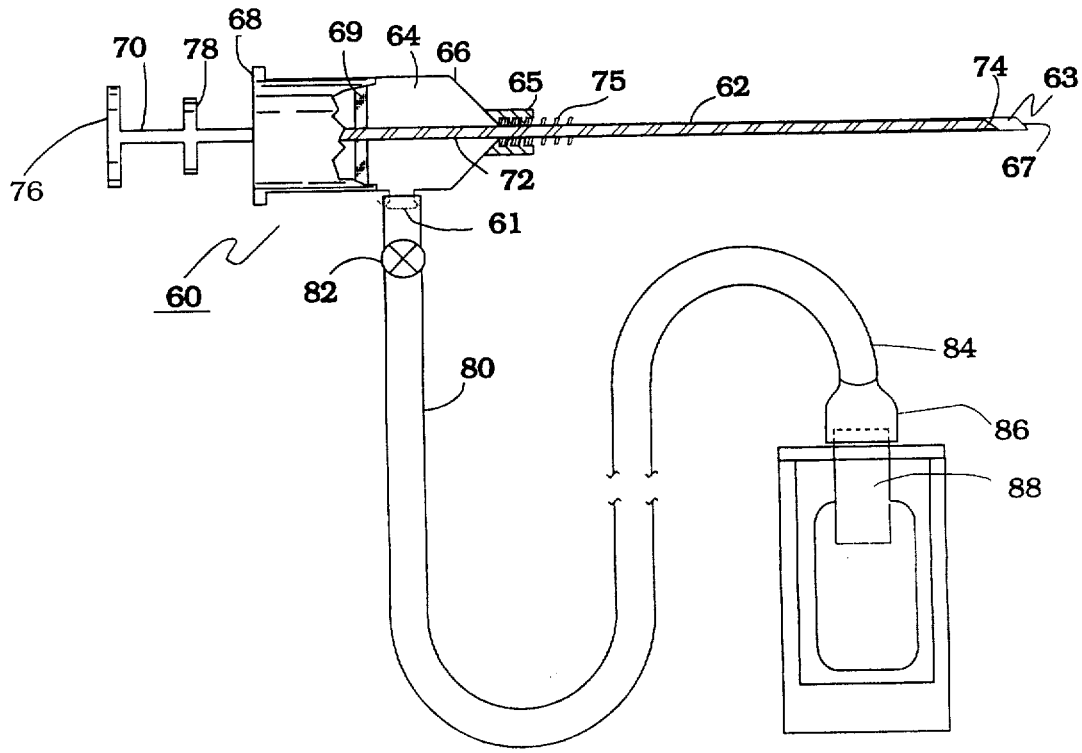

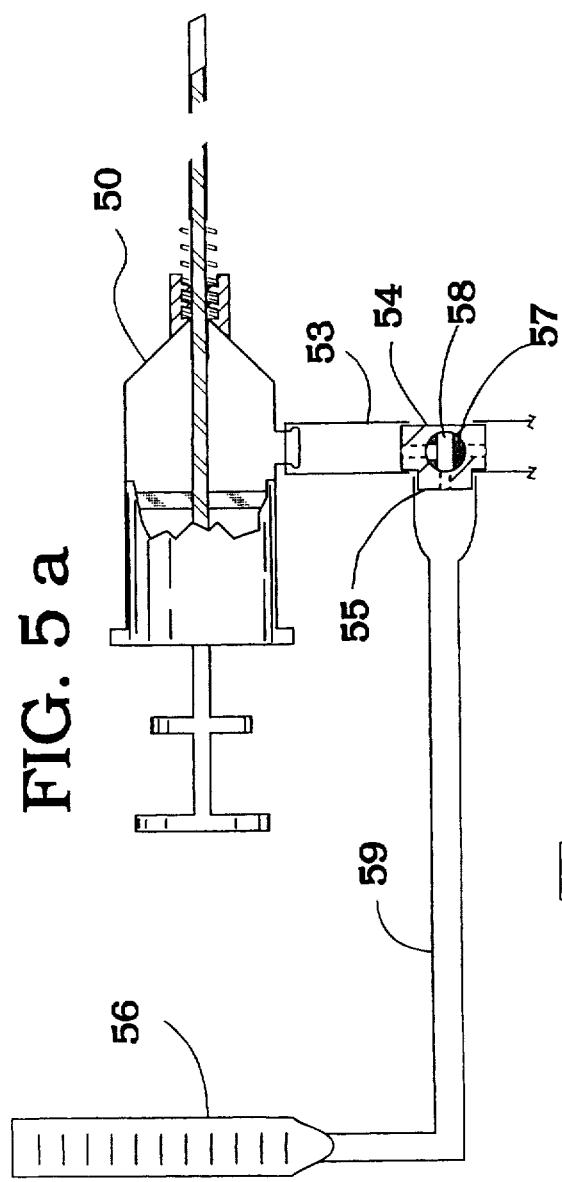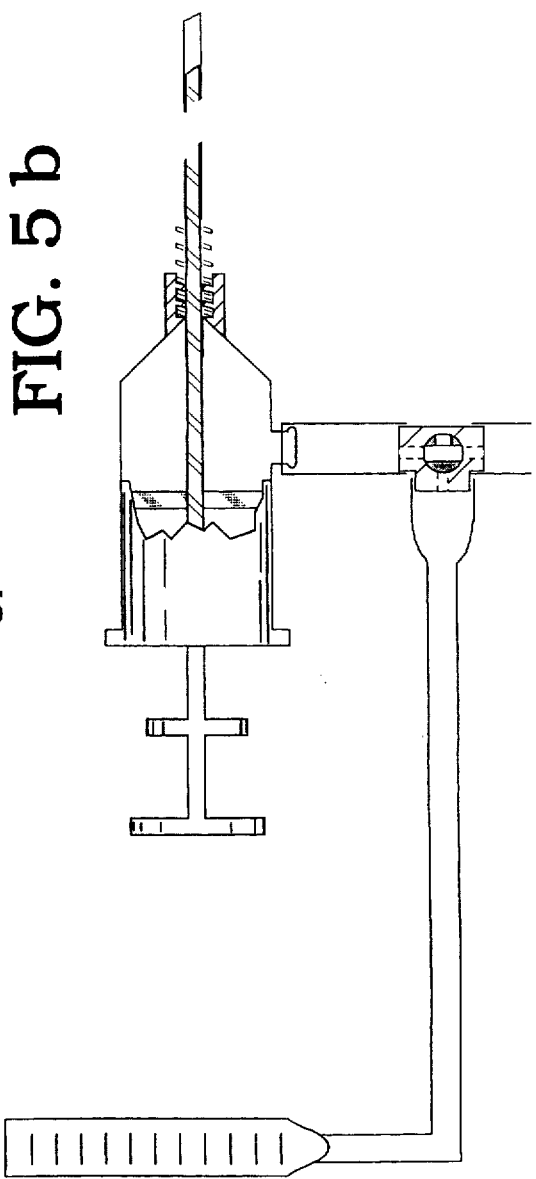

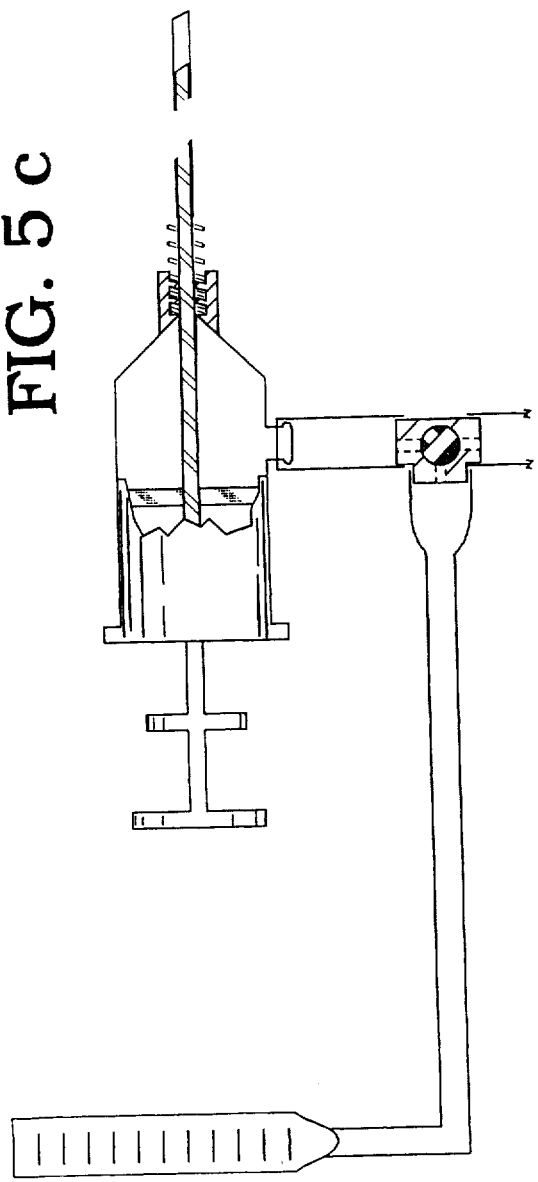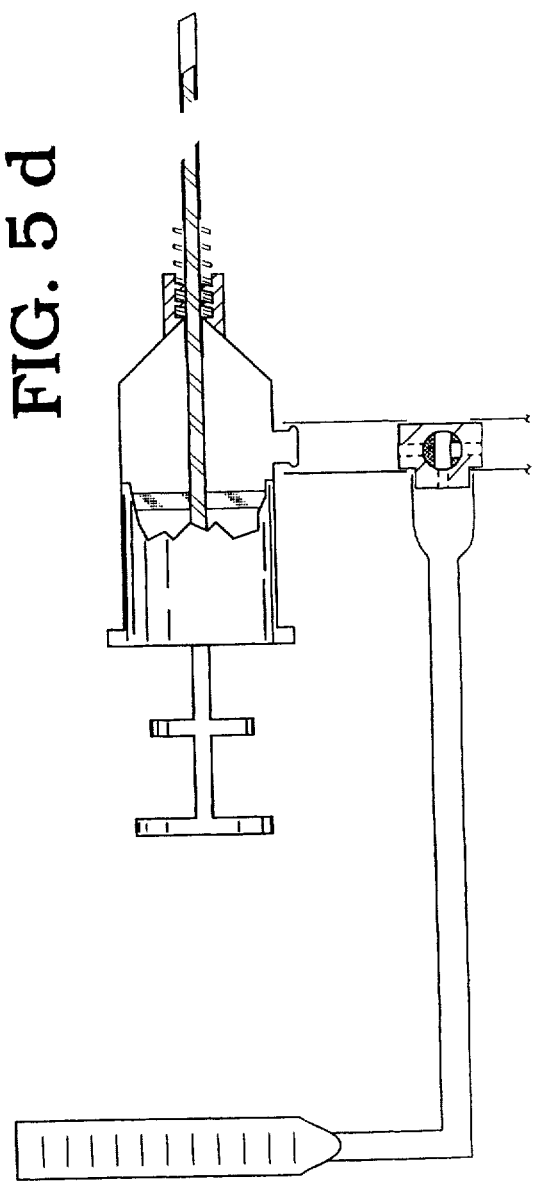

I claim:

1. In drawing from within a cavity of a patient's body of a sample of a cerebrospinal fluid for analysis, a sealed, non-subatmospheric pressure, fluid collection apparatus, comprising:
   (a) a sample container, comprising:
      a rigid, transparent sheath defining an enclosure vented to atmospheric pressure outside the rigid, transparent sheath; and
      an inflatable pouch to receive body fluid, the inflatable pouch including:
         a balloon within the enclosure defining an inner space and having an outer surface exposed to pressure within the enclosure and outside the inflatable pouch; the balloon being capable of free inflation within the enclosure as unpressurized body fluid drains by gravity in absence of other fluid motivation force into the inner space; and
         an inlet port joined to the balloon and in fluid communication with the inner space and adapted to provide a detachable, fluid tight connection to a source of supply of unpressurized body fluid, the inlet port being affixed to the rigid, transparent sheath;
   (b) a needle assembly adapted to communicate with the cavity and conduct body fluid outside the patient's body, the needle assembly including:
      a hollow barrel with an open end and a wall structure defining an interior volume to accept the body fluid;
      an elastomeric septum within the hollow barrel defining a puncturable, self-sealing, wall separating the interior volume from the open end;
      an outlet port on the wall structure and adapted to export body fluid from the interior volume;
   (c) a transfer tube having first and second ends, the transfer tube being close coupled at the first end in fluid communication with the outlet port, and the tube including at the second end an adapter means for detachably, fluid tightly connecting the second end to the sample container; and
   (d) a block valve between the cavity and the sample container for reversibly interrupting flow through the transfer tube.

2. The fluid collection apparatus of claim 1 wherein the needle assembly further comprises:
   a needle of strength and length effective to penetrate from outside the patient's body into the cavity, the needle having an axial bore communicating at a delivery end with the interior volume; and
   a stylet adapted to removably extend through the open end, to penetrate the elastomeric septum and to slidably insert into and withdraw from the axial bore, the stylet comprising
      a stylet rod having cross section shape and sufficient length to effectively fill the axial bore in a fully inserted position; and
      a handle at a stylet rod end to enable manipulation of the stylet.

3. The fluid collection apparatus of claim 1 wherein the transfer tube is integral to the outlet port.

4. The fluid collection apparatus of claim 1 wherein the transfer tube is of compressible, flexible material and the block valve is a pinch valve constricting the transfer tube to stop flow.

5. The fluid collection apparatus of claim 1 wherein the block valve includes a three-way rotatable stopcock in the transfer tube.

6. The fluid collection apparatus of claim 2 wherein the block valve includes a three-way, rotatable stopcock within the hollow barrel, the three-way rotatable stopcock having a through hole adapted to pass the stylet rod.

7. The fluid collection apparatus of claim 1 wherein the inlet port includes a puncturable, self-sealing, elastomeric cap and the adapter means includes a sharp male tubing nipple to pierce the elastomeric cap.

8. The fluid collection apparatus of claim 1 wherein the inlet port includes a tubular nipple extending outward from the rigid, transparent sheath and the adapter means includes a female receptacle to mate with the tubular nipple.

9. The fluid collection apparatus of claim 1 wherein the adapter means is a female, screw cap and the connector fitting is a male screw lip.

10. The fluid collection apparatus of claim 1 wherein the sample container further includes an identification color on a portion of the sheath.

11. The fluid collection apparatus of claim 1 wherein the inflatable pouch further comprises a discharge means on the balloon, for removing in a work area at least an inlet portion of the sample of body fluid from the container without biological agents present in the work area contaminating the sample without the body fluid contaminating the work area.

12. A method of drawing from within a patient's body cavity a sample of a cerebrospinal fluid for analysis, comprising the step of draining the fluid into a sample container including:
   a rigid, transparent sheath defining an enclosure vented to atmospheric pressure outside the sheath; and
   an inflatable pouch within the enclosure to receive body fluid, the pouch including:
      a balloon defining an inner space and having an outer surface exposed to pressure within the enclosure and outside the pouch; the balloon being capable of free inflation within the enclosure as unpressurized body fluid drains by gravity in the absence of other fluid motivation force into the inner space; and
      an inlet port affixed to the sheath and being adapted to releasably connect a supply of unpressurized body fluid to the inner space.

13. A process for drawing from within a cavity of a patient's body of a sample of a cerebrospinal fluid for analysis, comprising the steps of:
   I. connecting to a fluid collection apparatus, an empty sample container, comprising:
      (a) a rigid, transparent sheath defining an enclosure vented to atmospheric pressure outside the rigid, transparent sheath; and
      (b) an inflatable pouch to receive body fluid, the inflatable pouch including:
         (i) a balloon within the enclosure defining an inner space and having an outer surface exposed to pressure within the enclosure and outside the inflatable pouch; the balloon being capable of free inflation within the enclosure as unpressurized body fluid drains by gravity in absence of other fluid motivation force into the inner space; and (ii) an inlet port joined to the balloon and in fluid communication with the inner space, the inlet port being affixed to the rigid, transparent sheath;

wherein the inlet port is adapted to provide a detachable, fluid tight connection to a source of supply of unpressurized body fluid;

the fluid collection apparatus, comprising:

(A) a needle assembly adapted to communicate with the cavity and conduct body fluid outside the patient's body, the needle assembly including:
   (1) a hollow barrel with an open end and a wall structure defining an interior volume to accept the body fluid;
   (2) an elastomeric septum within the hollow barrel defining a puncturable, self-sealing, wall separating the interior volume from the open end; and
   (3) an outlet port on the wall structure and adapted to export body fluid from the interior volume;

(B) a transfer tube having first and second ends, the transfer tube being close coupled at the first end in fluid communication with the outlet port, and the tube including at the second end an adapter means for detachably, fluid tightly connecting the second end to the sample container; and (C) a block valve between the cavity and the sample container for reversibly interrupting flow through the transfer tube;

II. while holding the sample container below the elevation of the patient's body cavity, opening the block valve to let body fluid drain by gravity in the absence of other fluid motivation force into the sample container;

III. accumulating a predetermined amount of fluid sample in the sample container;

IV. closing the block valve to stop fluid flow into the sample container; and

V. disconnecting the sample container from the fluid collection apparatus.

14. The process of claim 13 wherein the needle assembly further includes:

a needle of strength and length effective to penetrate from outside the patient's body into the cavity, the needle having an axial bore communicating at a delivery end with the interior volume; and a stylet adapted to removably extend through the open end, to penetrate the elastomeric septum and to slidably insert into and withdraw from the axial bore, the stylet comprising a stylet rod having cross section shape and sufficient length to effectively fill the axial bore in a fully inserted position; and a handle at a stylet rod end to enable manipulation of the stylet; and wherein immediately after step 1, the process further comprises the steps of:

(I-1.) inserting the stylet completely through the open end of the hollow barrel and the elastomeric septum and into the axial bore of the needle;

(I-2.) performing a lumbar puncture of the patient; and (I-3.) removing the stylet from the needle to allow the body fluid to enter the interior volume of the hollow body.

15. The process of claim 13 wherein the unpressurized body fluid is cerebrospinal fluid.

16. The process of claim 14 wherein the unpressurized body fluid is cerebrospinal fluid.

* * * * *

UNITED STATES PATENT AND TRADEMARK OFFICE
CERTIFICATE OF CORRECTION

PATENT NO. : 5,772,607
DATED : Jun. 30, 1998
INVENTOR(S) : Magram

It is certified that error appears in the above-identified patent and that said Letters Patent is hereby corrected as shown below:

The title page should be deleted and substitute as per attached.

Drawing sheets 1-5 should be deleted and substituted with drawing sheets 1-5 as per attached.

Signed and Sealed this

Tenth Day of November 1998

Attest:

Attesting Officer

BRUCE LEHMAN

Commissioner of Patents and Trademarks

United States Patent [19]

Magram

[11] Patent Number: 5,772,607
[45] Date of Patent: Jun. 30, 1998

[54] BODY FLUID COLLECTION APPARATUS

[75] Inventor: Gary Magram, Greenville, Del.

[73] Assignee: The Nemours Foundation, Jacksonville, Fla.

[21] Appl. No.: 471,274

[22] Filed: Jun. 6, 1995

[51] Int. Cl.$^6$ .................................................. A61B 5/00
[52] U.S. Cl. ................................................................ 600/573
[58] Field of Search ........................................ 604/118, 128, 604/246, 326, 164, 167, 317, 318, 319, 403, 410, 411; 128/76–771

[56] References Cited

U.S. PATENT DOCUMENTS

| | | | |
|---|---|---|---|
| 3,654,924 | 4/1972 | Wilson et al. | 128/214 D |
| 3,704,709 | 12/1972 | Sorenson et al. | 128/277 |
| 3,785,367 | 1/1974 | Fortin et al. | 128/2 F |
| 3,957,050 | 5/1976 | Hines, Jr. | 128/275 |
| 4,060,107 | 11/1977 | Naftulin | 141/7 |
| 4,522,623 | 6/1985 | Lauterjung | 604/319 |
| 4,645,486 | 2/1987 | Beal et al. | 604/4 |
| 4,675,010 | 6/1987 | Siposs et al. | 604/319 |
| 5,122,121 | 6/1992 | Sos et al. | 604/167 |
| 5,167,656 | 12/1992 | Lynn | 604/409 |
| 5,207,661 | 5/1993 | Repschlager | 604/317 |

Primary Examiner—Max Hindenburg
Assistant Examiner—Pamela L. Wingood
Attorney, Agent, or Firm—J. Michael Martinez de Andino; McGuire, Woods, Battle & Boothe LLP; Jeffrey C. Lew

[57] ABSTRACT

A sample container and a fluid collection apparatus are disclosed for withdrawing samples for fluid analysis purposes of unpressurized body fluid from an internal body cavity. The container and apparatus are primarily useful for sampling cerebrospinal fluid obtained through a lumbar puncture or shunt tap. The container and apparatus provide a completely enclosed sample environment which protects the sample from external contamination during the sample-taking process. The enclosed environment also protects sample-taking personnel against direct contact with the fluid. The novel sample container includes an inflatable pouch with a balloon that expands on filling without significantly raising back pressure on the fluid draining from the patient. The pouch is affixed within a transparent, rigid sheath by an inlet port. The apparatus includes a needle assembly with an internal rubber septum. The septum prevents fluid from leaking out when a stylet is removed from the needle bore after the lumbar puncture is performed.

16 Claims, 5 Drawing Sheets